United States Patent
Narducci et al.

(10) Patent No.: US 8,388,622 B2
(45) Date of Patent: Mar. 5, 2013

(54) SURGICAL FILE INSTRUMENT CONSTRUCTION WITH MECHANISM TO CONVERT ROTARY MOTION TO RECIPROCAL MOTION

(75) Inventors: David Narducci, Lake Worth, FL (US); Stephen Bucina, Cocoa Beach, FL (US); Michael Menard, Boynton Beach, FL (US); Eddy H. Del Rio, Royal Palm Beach, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 662 days.

(21) Appl. No.: 12/586,091

(22) Filed: Sep. 17, 2009

(65) Prior Publication Data

US 2011/0066154 A1 Mar. 17, 2011

(51) Int. Cl.
    *A61B 17/00* (2006.01)
(52) U.S. Cl. .......................................... 606/85
(58) Field of Classification Search .................... 606/84, 606/85
    See application file for complete search history.

(56) References Cited

U.S. PATENT DOCUMENTS

| | | | |
|---|---|---|---|
| 4,827,616 A | 5/1989 | Sistare | |
| 4,940,061 A | 7/1990 | Terwilliger | |
| 5,411,513 A | 5/1995 | Ireland | |
| 5,833,704 A | 11/1998 | McCombs et al. | |
| 5,993,454 A * | 11/1999 | Longo | 606/80 |
| 6,048,345 A * | 4/2000 | Berke et al. | 606/85 |
| 6,286,611 B1 * | 9/2001 | Bone | 173/216 |
| 6,485,495 B1 * | 11/2002 | Jenkinson | 606/84 |
| 6,610,066 B2 | 8/2003 | Dinger et al. | |
| 7,390,330 B2 | 6/2008 | Harp | |
| 7,666,186 B2 * | 2/2010 | Harp | 606/85 |
| 2005/0252670 A1 | 11/2005 | Prell et al. | |
| 2006/0206117 A1 | 9/2006 | Harp | |
| 2011/0066155 A1 * | 3/2011 | Del Rio et al. | 606/85 |

FOREIGN PATENT DOCUMENTS

WO   WO 2008/058157   5/2008

* cited by examiner

*Primary Examiner* — Nicholas Woodall
(74) *Attorney, Agent, or Firm* — Meunier Carlin & Curfman, LLC

(57) ABSTRACT

A surgical file instrument comprising a file, file guide, an outer split casing, a motion converter converting rotary motion to reciprocal motion and file assembly. The file assembly consists of an angular shaped elongated tube fairing into a generally flat portion defining the guide for the blade of the file, a complementary shaped file and a plastic rod insert having a lumen for the file and a lumen defining a passage for flowing a fluid to the surgical site. The motion converter consists of a planetary gear system connected to the battery powered motor that rotates a platen which in turn drives a cam and cam follower fitted into the cam slot for driving a drum for producing rectilinear motion. The file assembly is attached to the drum for reciprocating the file blade for use in a medical procedure for removing bone or a portion thereof.

11 Claims, 5 Drawing Sheets

SURGICAL FILE INSTRUMENT CONSTRUCTION WITH MECHANISM TO CONVERT ROTARY MOTION TO RECIPROCAL MOTION

RELATED APPLICATIONS

This application relates to the contemporaneously filed patent application entitled "SURGICAL FILE" and invented by Eddy Del Rio, David Narducci, and Michael Menard Ser. No. 12/586,092 and assigned to the same assignee as the present application and incorporated herein in its entirety by reference.

FEDERALLY SPONSORED RESEARCH OR DEVELOPMENT

Not applicable

BACKGROUND OF THE INVENTION

1. Field of the Invention

This invention relates to a surgical file that is used in a surgical procedure for removing bone or portions thereof from a patient. More particularly, the invention relates to a surgical file for cutting, removing, grinding, shaping and sculpturing bone and to the surgical file construction and the mechanism for imparting reciprocal motion to the reciprocating file of the surgical instrument.

2. Description of Related Art

U.S. Pat. No. 7,390,330 granted to Harp on Jun. 24, 2008 describes a surgical file that has a sundry of applications that may be used by a surgeon for the treatment of certain types of pathology. Essentially, this patent relates to a surgical file that is similar to the surgical file described in the present patent application and the invention described in this patent application patentably distinguishes over the surgical file disclosed in the U.S. Pat. No. 7,390,330 patent ('330), supra while also, obtaining unexpected results for the reasons that will be described herein below. The '330 patent, supra, discloses a shielded reciprocating surgical file system and allows a user to navigate the file into hard to access parts of the patient's body. A transmission mechanism converts rotary motion from a motor into reciprocating motion and pump mechanism and an irrigation system that supplies fluid to the surgical site.

To obtain the reciprocal motion from the rotary motion, the structure disclosed in the '330 patent, supra, utilizes a torus transmission device which may include an integral shaft or a rigidly connected shaft. The torus drive and drive shaft are rotatable about a central rotation axis and has a generally circular or curvilinear cam portion with the torus central axes being at an offset angle. The variable thickness of the torus cam surface produces a hybrid dual or twin torus. As will become evident from the description to follow, the inventive mechanism described in this application provides a far less complicated transmission system for converting the rotary motion to reciprocal motion as will be described in more detail herein below.

The file member of the surgical file instrument includes an elongated angular shaft portion having a blade on the distal end and a tang on the proximal end and is encapsulated in an elongated cylindrical tube of plastic material disposed in an elongated generally "infinity symbol" shaped aperture and having lumens formed therein. The lumens serve to define passageways extending externally of the patient to the surgical site. The distal end of the elongated tube flairs into a generally flat portion with judicious located curvatures that together define a guide for the blade of the file.

As was discussed in the '330 patent, supra, the present invention has utility for many medical procedures that are typically the concern in neurosurgery, orthopedic surgery and plastic surgery, amongst others. For example in neurosurgery, the neruroforamen may need enlargement and the file can be instrumental in removing rigid bony vertebral structure to allow the nerve roots to pass there through. In orthopedic surgery the knee may require sculpturing. And, in plastic surgery bone and tissue sculpturing may be required for nose reshaping and rhinoplasty. The surgical file is efficacious for use in these types of procedures and methodology.

SUMMARY OF THE INVENTION

An object of this invention is to provide an improved surgical file.

A feature of this invention is to provide for a surgical file an improved mechanism for converting rotary motion to reciprocal motion and is characterized as being compact and efficacious in operation, contributes to the minimal size of the instrument and enhances the feel while being used by a surgeon Another feature of this invention is the utilization of a planetary gear system for implementing the conversion of rotary to reciprocal motion.

Another feature of this invention is the utilization of thrust pins operably connected to the cylindrical cam and grounded to the surgical instrument casing.

Another feature of this invention is the utilization of a cylindrical cam with a single follower and drum combination.

Another feature of this invention is the utilization of a solid rod made from a plastic material mounted in an outer tubular casing including an elongated central aperture for the file assembly and lumen for defining passageways exterior of the surgical file instrument extending to the surgical site.

Another feature of this invention is that the elongated central aperture for supporting the file of the file assembly is shaped in a configuration resembling the infinity symbol.

The foregoing and other features of the present invention will become more apparent from the following description and accompanying drawings

DETAILED DESCRIPTION OF THE INVENTION

As will be appreciated by those skilled in this technology, the configuration of the file assembly and particularly to the blade and tang may take many different forms and designs without departing from the scope of the invention. For example, the dimensions of the angles of the file assembly may be different or non-angularly shaped, the types of blade of the file may be different from the one depicted in the preferred embodiment.

Figure 1:
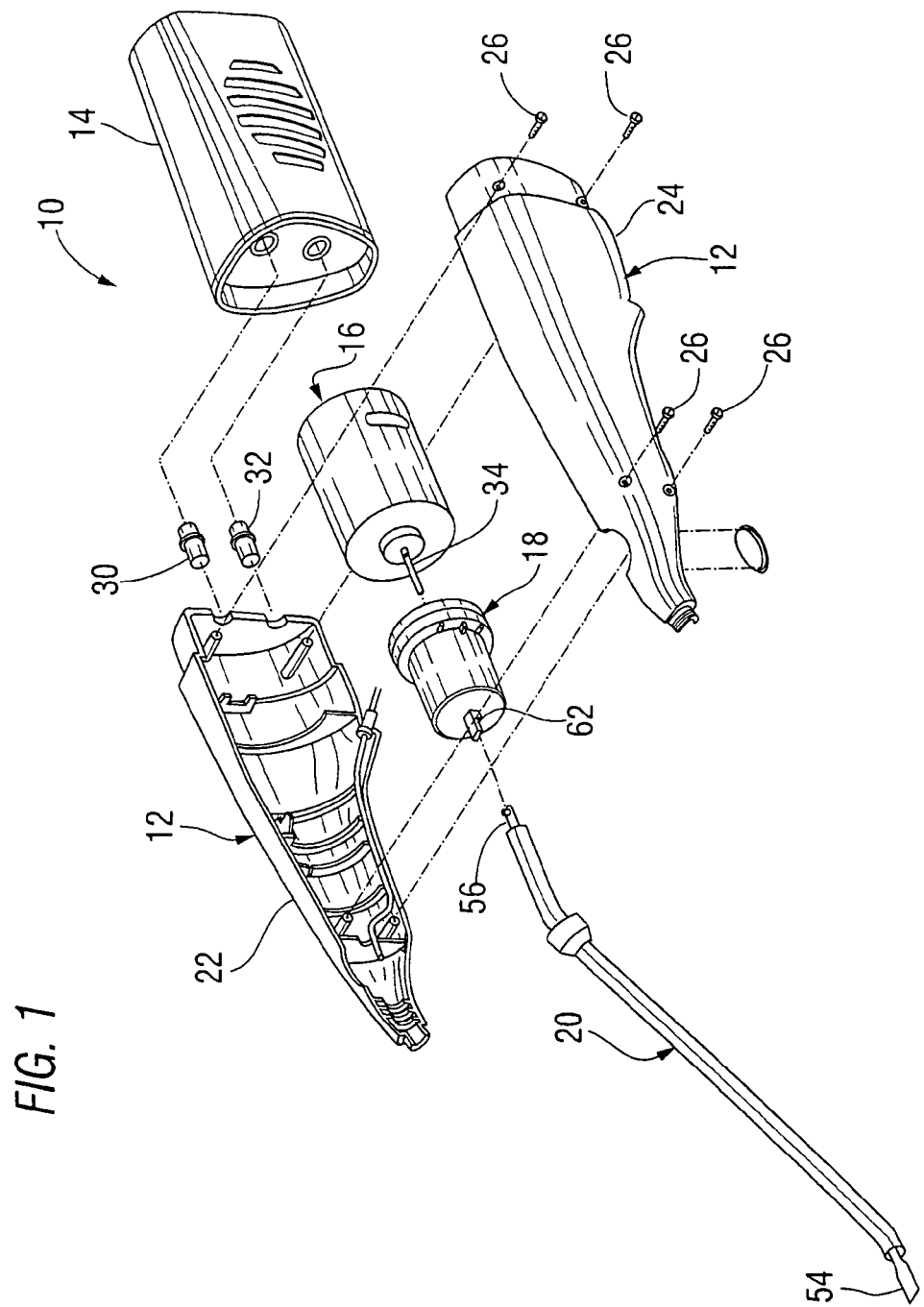
FIG. 1 is an exploded view in perspective illustrating the invention.
Figures 2, 2A:
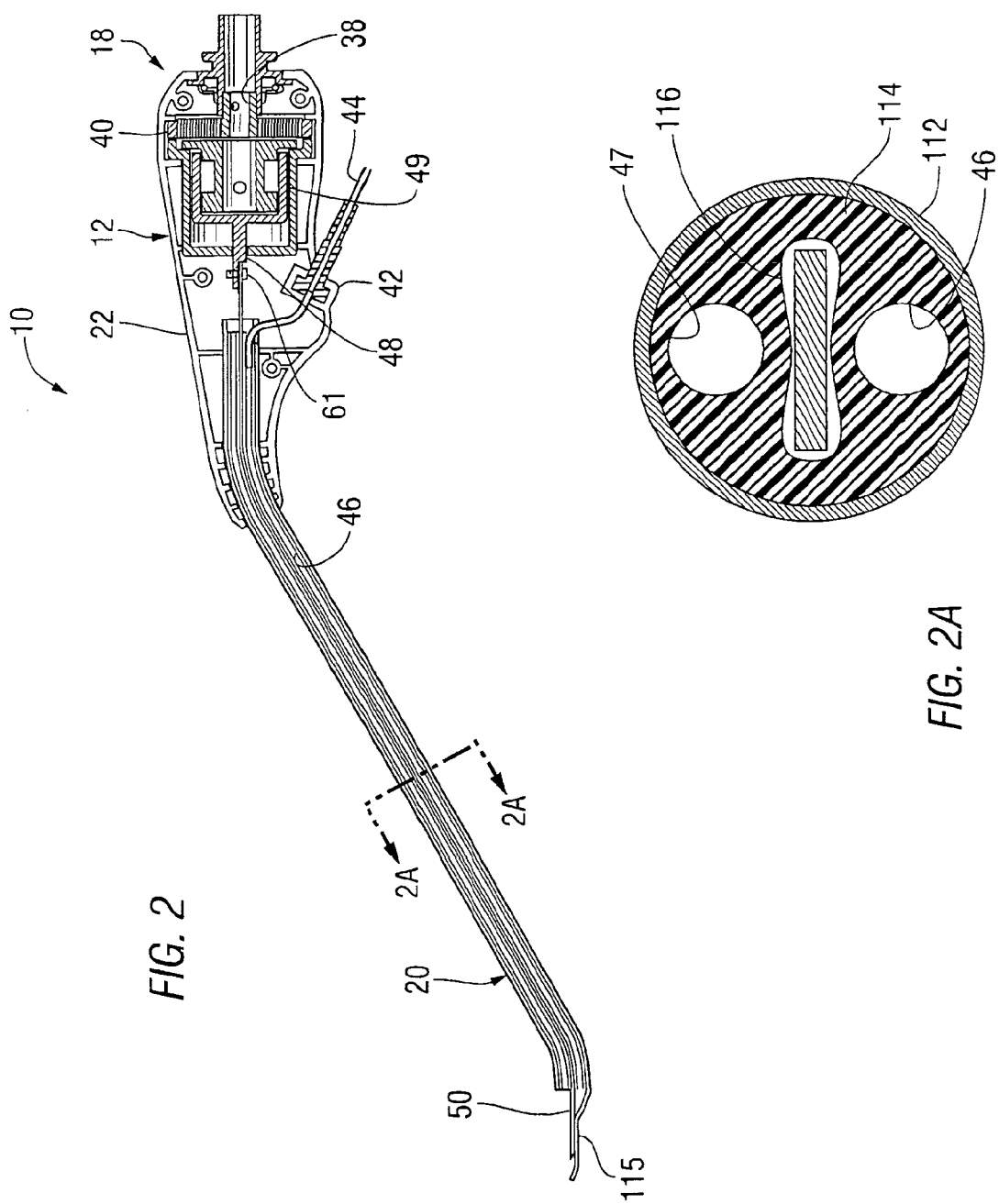
FIG. 2 is an assembled a sectional view of the surgical file instrument of this invention.
FIG. 2A is a sectional view taken along lines 2A-2A in FIG. 2.
Figure 4:
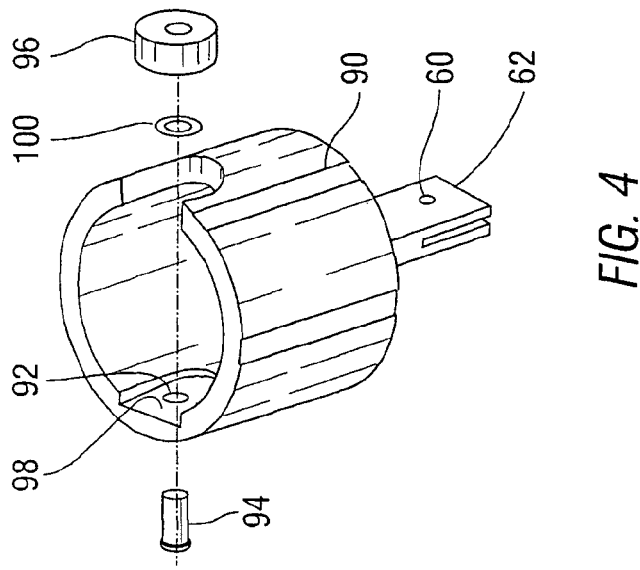
FIG. 4 is an enlarged view in perspective of the drum depicted in FIG. 3.
Figure 3:
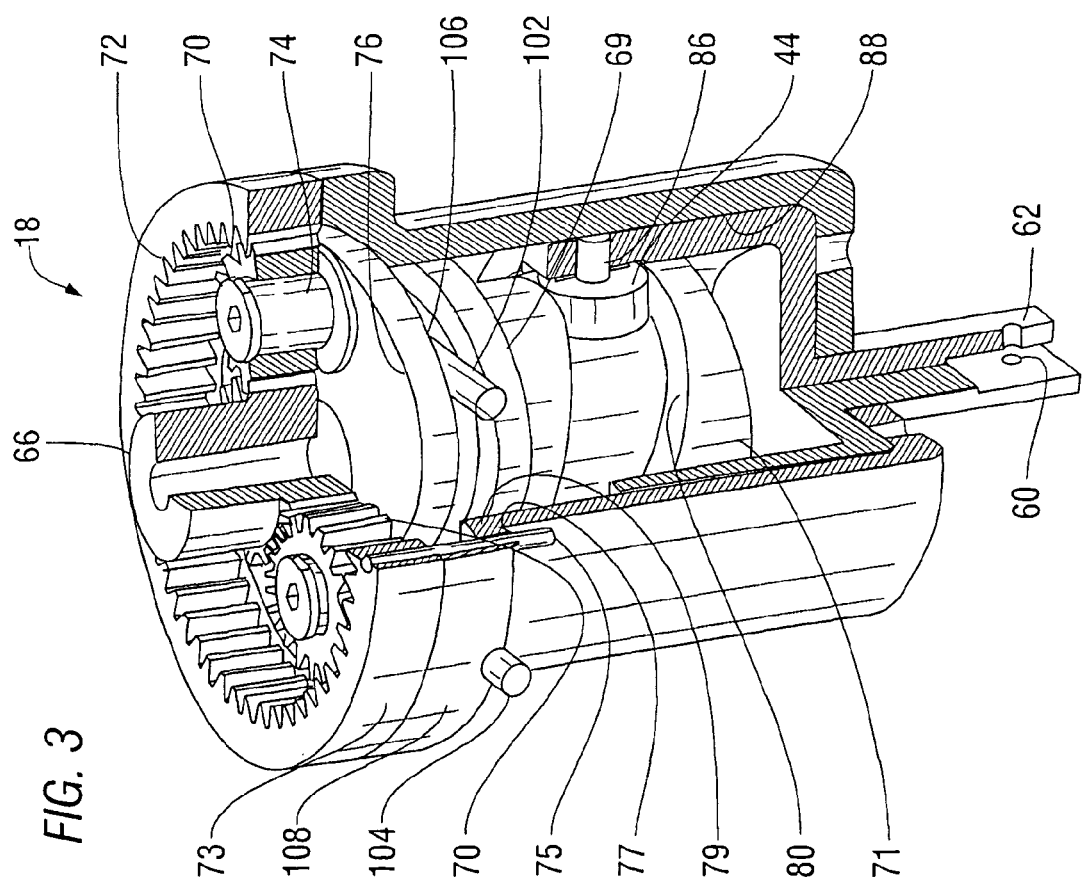
FIG. 3 is a partial enlarged view in perspective and section illustrating the motion converter of this invention.

The invention can best be seen by referring to FIGS. 1-4 which show the surgical file instrument generally illustrated by reference numeral 10 comprising the outer split casing 12, the battery 14, electric motor 16, the motion converter 18, and the file assembly 20. In the assembled condition as seen in FIG. 2, the casing 12 is formed in two generally cylindrical members 22 and 24 that are suitably attached by the screws 26 threadably engaging the threaded lugs 28. The terminals 30 and 32 connect the motor 16 to the battery 14 for powering the motor and driving drive shaft 34. In turn, the drive shaft 34 provides rotary motion to the motion converter 18, as will be described in detail herein below. As noted in FIG. 2, the drive shaft 34 is coupled to the driven shaft 38 of the planetary system 40 of the motion converter 18 for rotating the same. As will be explained below, the planetary gear system 40 rotates the cam 71 and via the follower 44 (see FIG. 3), which, in turn, translate the drum 49 and shaft 48 to impart reciprocal motion.

Figure 5:
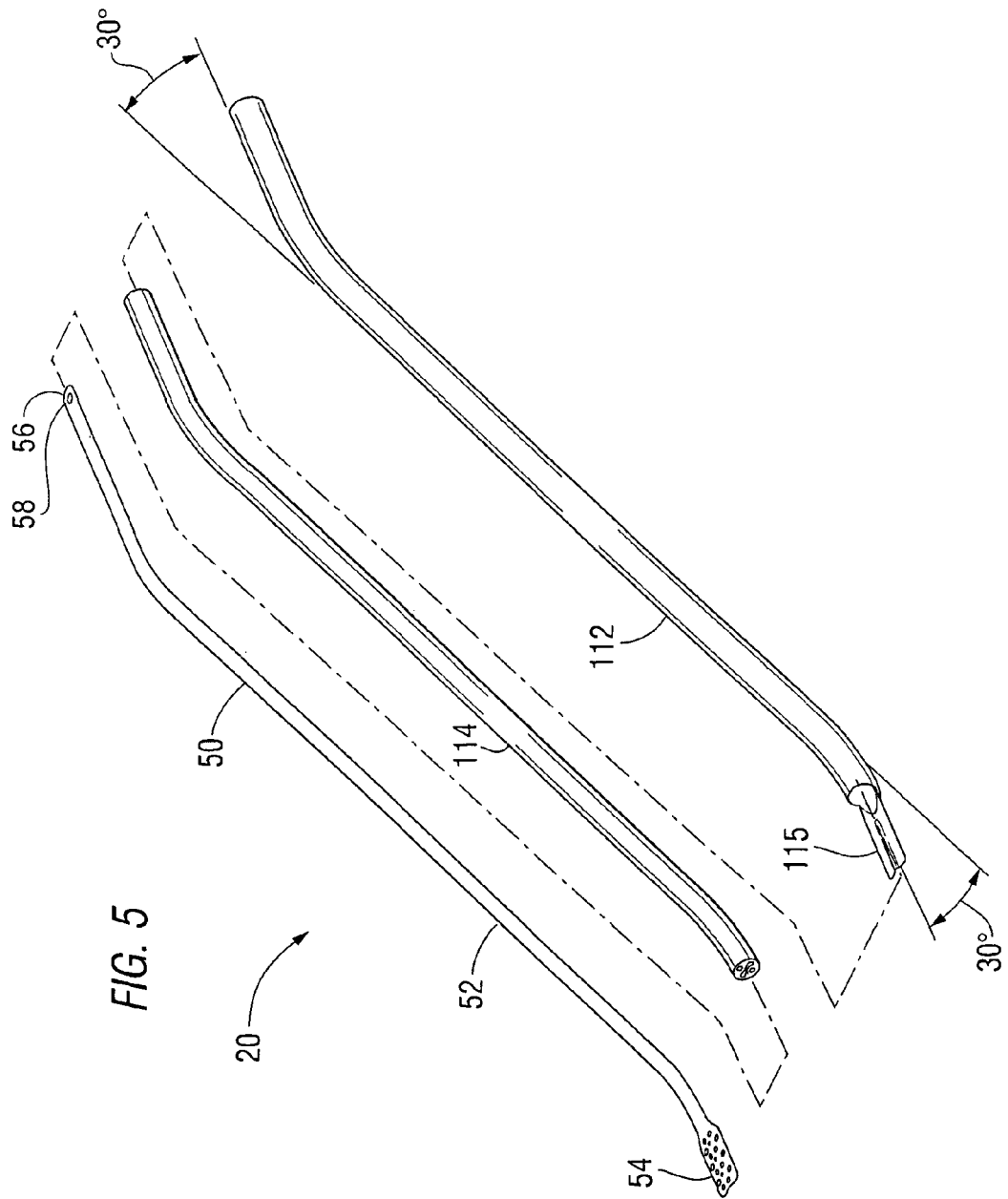
FIG. 5 is an exploded view in elevation illustrating the file assembly of this invention.

The file assembly 20 (see FIG. 5) includes the file 50 having an angular shaft 52, a blade 54 and tang 56. Tang 56 includes hole 58 (see FIG. 5) that cooperates with a complementary threaded hole 60 formed in the end portion 62 and with a suitable bolt 61 fitted into hole 58 is threaded to hole 60 connects the file 50 to drum 49 for imparting reciprocation to the file 50.

It is typical in this type of instrument to provide irrigation to the surgical site. To this end, the casing 12 includes port 42 and the lubricant transmittal tube 44 that is connected to the lumen 46 formed in the file assembly 20.

The next portion of this application will describe the inventive cam/drum configuration of the motion converter 18. The pinion gear 68 is directly coupled to the drive shaft 34 of motor 16. Pinion gear 68, in turn, meshes with each of the planetary gears 70, (three in number) which, in turn, meshes with the fixed ring gear 72. Ring gear 72 in its preferred embodiment is formed integrally by molding it to the outer casing 73. Alternatively ring gear 72 may be fixed to the outer casing 73 via the dowel pin 75 disposed in the slot 77 formed in the flange 79. As is apparent from FIG. 3, each of the planetary gears 70 are rotary supported to stub shaft 74 which is suitably pinned to platen 76. Platen 76 is a portion of the rotating cam 78 which is rotated by the spinning planetary gears 70. Cam 78 includes the main body 71 that has formed therein the cam slot 80 that is designed to produce reciprocal motion as will be apparent from the following description. Follower 84 fitted into the cam slot 80 is pinned via pin 86 to drum 88. As noted, and in accordance with this invention, a single cam follower is all that is necessary to drive drum 88. Drum 88 comprises the hollow sleeve 90 (see FIG. 4) having the aperture 92 formed on the peripheral side thereof. The follower 44 consists of stub shaft 94 locks roller 96 to the hollow sleeve 90 via the recess 98. A washer 100 may be used to assure that the roller has sufficient spacing so that its rolling around shaft 94 is not impaired. In accordance with this invention, two (2) thrust pins 102 and 104 fit into annular groove 106 formed in the cam. The thrust pins 102 and 104 are grounded to the cam casing 108

In operation, the motor drives pinion gear 68 which, in turn, meshes with the three (3) planetary gears 70 which, in turn, meshes with the fixed ring gear 72. This re-action of all of the above mentioned gears rotates the cam 69 via the platen 76 that is formed integral with the cam 69, and, as a consequence, rotates therewith. This rotary motion, in turn, is converted to reciprocal motion via the follower 44 that drives the drum rectilinearly which defines the reciprocal motion. Obviously, this motion is translated to the file by the connection described above.

Also, in accordance with this invention, the file is unique as will be described in detail herein below. As mentioned above the file assembly comprises an outer tube or tubular casing 112 that has integrally formed thereon at the distal end a flat and angular shaped shield and guide member 115. The solid tubular insert 114, resembling a rod, is tightly fitted into tube 112 and formed within the tubular insert 114 are the "infinity-shaped" slot 116 and a pair of lumens 46 and 47. (See FIG. 2A) The generally flat file 50 fits into the infinity slot 116 and extends beyond the distal end of the solid rod 114 and is contiguous to the upper surface of the guide portion 115 and slides in rectilinearly thereon. In its preferred embodiment, the file assembly is bent 30 degrees adjacent to the proximal end and the same angle adjacent to the distal end. Obviously, the particular shape of the file assembly will be predicated on the particular use given the surgical file instrument.

Figure 6:
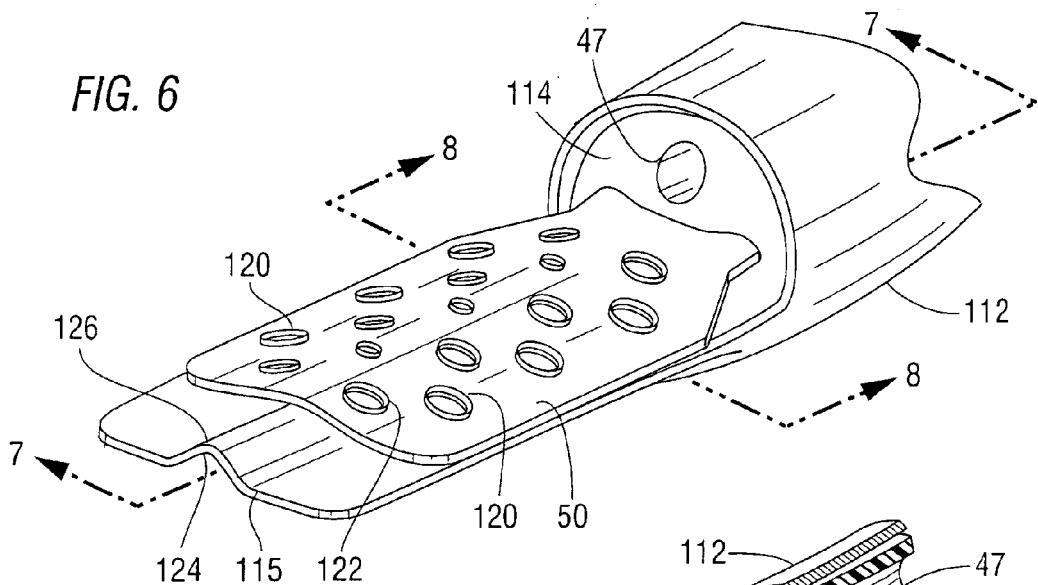
FIG. 6 is an enlarged partial view in perspective of the file, the file blade, the file shield and the file assembly.
Figure 7:
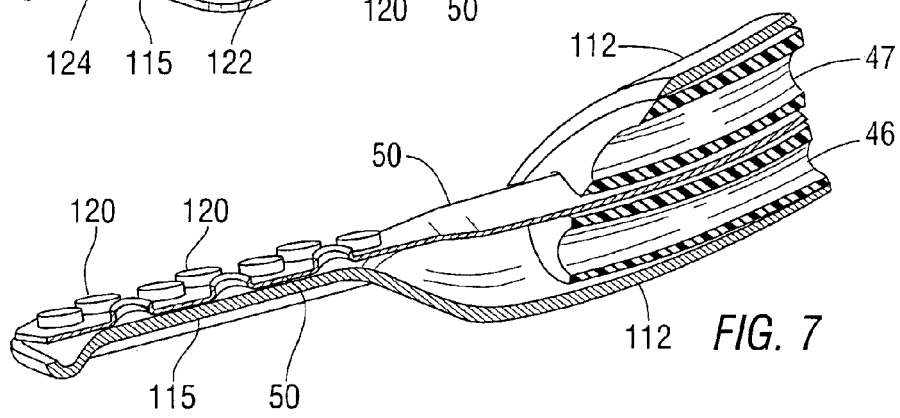
FIG. 7 is a sectional view taken along lines 7-7 of FIG. 6.
Figure 8:
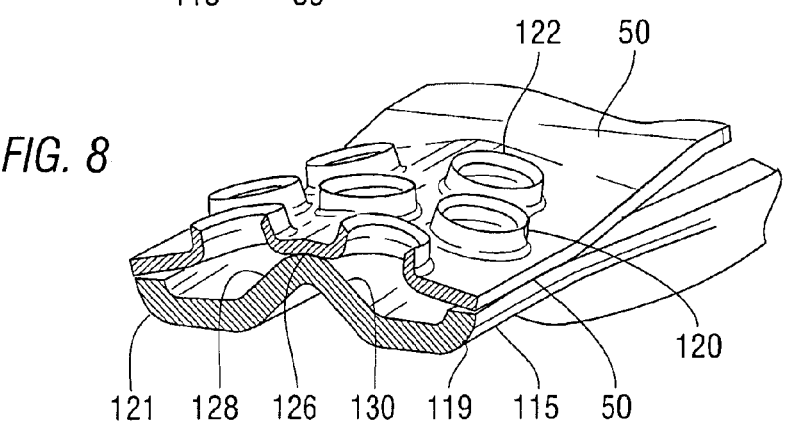
FIG. 8 is a sectional view taken along lines 8-8 of FIG. 6.

As shown in FIGS. 6-8, the cutting surface of the blade 50 consists of a plurality of radial projecting ring-like elements 120 that serve as cutting edges 122. As mentioned earlier, the particular file head is not a concern of this invention. However, of importance is the shape of the shield 115 which is located at the distal end of tube 112. The shield 115 is formed at the distal end of the outer tube 112 that flairs into a generally flat portion 117 with the side edges 119 and 121 upturned to engage the side edges on the under surface of the blade 50. Formed on shield 115 is the elongated dimple 124 extending longitudinally along the central portion of shield 115. The dimple includes the apex 126 and the straight slopes 128 and 130 extending from either sides there of. This particular configuration centers the file and keeps it motion in a linear straight line which obviously, is important for the delicate types of operation to which the surgical file instrument is used. The lower portion of the shield 115 extends radial toward the outer edges of file 50 and is bent slightly upwardly to be in contiguous contact with the side edges of file 50 as described above and together with the dimple 124 the blade 50 rides in a true line during its reciprocating condition.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A surgical file instrument comprising a tubular casing supporting a reciprocating surgical file,
   said reciprocating surgical file having a blade at the distal end and a tang at its opposite end,
   a solid tubular member supported in said tubular casing having an elongated lumen for receiving said reciprocating surgical file wherein said blade is located at the distal end thereof and projects there-beyond and said tang is located at the proximal end thereof and projects there-beyond,
   a motion converter comprising a split housing,
   said motion converter including means in said split housing for converting rotary motion to reciprocal motion,
   a rotary motor in said split housing,
   said means including a planetary gear system driven by said motor,
   a drum, a cam having a cam slot operatively connect to said planetary gear system and a cam follower attached to the outer periphery of said drum wherein the cam rotated by the planetary gear system rotary positions the cam slot such that the cam follower imparts reciprocal motion to said drum, a shaft attached to one end of said drum and being attached to said tang for imparting reciprocal motion to said blade, and a source of power for powering said motor for causing said blade to reciprocate.

2. A surgical file instrument as claimed in claim 1 including an annular slot formed in said cam, at least one thrust pin extending from said split housing extending into said annular slot for absorbing thrust loads imposed on said cam.

3. A surgical file instrument as claimed in claim 2 including a platen on one end of said cam, a plurality of shafts circumferentially spaced around said platen and attached thereto, a gear attached to each of said shafts for imparting rotary motion to said platen.

4. A surgical file instrument as claimed 2 wherein said source of power is a battery.

5. A surgical file instrument as claimed 3 said surgical file instrument includes a tubular casing encapsulating said solid tubular member.

6. A surgical file instrument as claimed 5 wherein said elongated lumen is shaped like an infinity symbol.

7. A surgical file instrument as claimed in claim 5 wherein said tubular casing includes a flattened portion formed on the distal end and being adjacent to said blade and defining a combined guide and shield member.

8. A surgical file instrument comprising a tubular casing supporting a reciprocating surgical file, said reciprocating surgical file having a blade at the distal end and a tang at its opposite end, a solid tubular member supported in said tubular casing having an elongated lumen for receiving said reciprocating surgical file wherein said blade is located at the distal end thereof and projects there-beyond and said tang is located at the proximal end thereof and projects there-beyond, a tubular casing partially encapsulating said solid tubular member, a motion converter comprising a split housing, said motion converter including means in said split housing for converting rotary motion to reciprocal motion, a rotary motor in said split housing, said means including a planetary gear system driven by said motor, a drum, a cam having a cam slot and a cam follower in said cam slot operatively connected to said planetary gear system and operatively connected to said drum for reciprocating said drum, a shaft attached to one end of said drum and being attached to said tang for imparting reciprocal motion to said blade, an annular slot formed in said cam, a pair of diametrically opposed thrust pins extending from said split housing extending into said annular slot for absorbing thrust loads imposed on said cam, and a source of power for powering said motor for causing said blade to reciprocate.

9. A surgical file instrument as claimed in claim 8 including an annular slot formed in said cam, at least one thrust pin extending from said split housing extending into said annular slot for absorbing thrust loads imposed on said cam, a platen on one end of said cam, a plurality of shafts circumferentially spaced around said platen and attached thereto, a gear attached to each of said shafts for imparting rotary motion to said platen.

10. A surgical file instrument as claimed 9 wherein said surgical file instrument includes a tubular casing encapsulating said solid tubular member, said elongated lumen is shaped like an infinity symbol, said tubular casing includes a flattened portion formed on the distal end and being adjacent to said blade and defining a combined guide and shield member.

11. A surgical file instrument comprising a tubular casing supporting a reciprocating surgical file, said reciprocating surgical file having a blade at the distal end and a tang at its opposite end, a solid tubular member supported in said tubular casing having an elongated lumen for receiving said reciprocating surgical file wherein said blade is located at the distal end thereof and projects there-beyond and said tang is located at the proximal end thereof and projects there-beyond, a motion converter comprising a split housing, said motion converter including means in said split housing for converting rotary motion to reciprocal motion, a rotary motor in said split housing, said means including a planetary gear system driven by said motor, a drum, a cam having a cam slot and a cam follower in said cam slot operatively connected to said planetary gear system and operatively connected to said drum for reciprocating said drum, a shaft attached to one end of said drum and being attached to said tang for imparting reciprocal motion to said blade, and a source of power for powering said motor for causing said blade to reciprocate, an annular slot formed in said cam, at least one thrust pin extending from said split housing extending into said annular slot for absorbing thrust loads imposed on said cam, a platen on one end of said cam, a plurality of shafts circumferentially spaced around said platen and attached thereto, a gear attached to each of said shafts for imparting rotary motion to said platen, a tubular casing encapsulating said solid tubular member, said elongated lumen is shaped like an infinity symbol, said tubular casing includes a flattened portion formed on the distal end and being adjacent to said blade and defining a combined guide and shield member, wherein said source of power is a battery.

* * * * *